United States Patent
Lazzara et al.

[11] Patent Number: 6,129,548
[45] Date of Patent: *Oct. 10, 2000

[54] TWO-PIECE HEALING ABUTMENT SYSTEM

[75] Inventors: Richard J. Lazzara, Lake worth; Keith D. Beaty, Jupiter, both of Fla.; Curtis E. Jansen, Pacific Grove, Calif.

[73] Assignee: Implant Innovations, Inc., Palm Beach Gardens, Fla.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/837,379

[22] Filed: Apr. 17, 1997

Related U.S. Application Data

[62] Division of application No. 08/527,508, Sep. 13, 1995, Pat. No. 5,674,071, which is a continuation of application No. 08/248,497, May 24, 1994, abandoned, which is a continuation of application No. 08/043,928, Apr. 8, 1993, Pat. No. 5,338,196.

[51] Int. Cl.[7] .................................................. A61C 8/00
[52] U.S. Cl. ............................................ 433/172; 433/173
[58] Field of Search .................................... 433/172, 173, 433/174, 175, 214

[56] References Cited

U.S. PATENT DOCUMENTS

| | | |
|---|---|---|
| 4,086,701 | 5/1978 | Kawahara et al. . |
| 4,758,161 | 7/1988 | Niznick ................................ 433/173 |
| 4,842,518 | 6/1989 | Linkow et al. ......................... 433/174 |
| 4,850,870 | 7/1989 | Lazzara et al. ........................ 433/173 |
| 4,850,873 | 7/1989 | Lazzara et al. ........................ 433/220 |
| 4,856,994 | 8/1989 | Lazzara et al. ........................ 433/173 |
| 4,955,811 | 9/1990 | Lazzara et al. ........................ 433/173 |
| 4,988,298 | 1/1991 | Lazzara et al. ........................ 433/173 |
| 5,000,685 | 3/1991 | Brajnovic .............................. 433/173 |
| 5,006,069 | 4/1991 | Lazzara et al. ........................ 433/173 |

(List continued on next page.)

FOREIGN PATENT DOCUMENTS

| | | |
|---|---|---|
| 0 442 855 | 8/1991 | European Pat. Off. . |
| 1291470 | 10/1972 | United Kingdom . |

OTHER PUBLICATIONS

Deposition transcript of Dr. Fereidoun Daftary dated Aug. 21, 1998 and associated exhibits.
Documents produced by Dr. Fereidoun Daftary (FD2–498), various dates (documents FD1, FD102–106, FD226, FD379, FD380 not in Applicants' possession due to claim of Attorney–Client Privilege by Dr. Daftary).
Exhibit A, a drawing of a healing abutment.
Exhibit B, an assembly drawing of a coping and the component drawings which comprise the coping assembly.
Lewis, S.G. et al., *Single Tooth Implant Supported Restorations*, Intnatl. Jrnl. of Oral & Maxillofacial Implatns, vol. 3, No. 1, pp. 25–30, 1988.
Lewis, S.G. et al., *The "UCLA" Abutment*, Intnatl. Jrnl. of Oral & Maxillofacial Implants, vol. 3, No. 3, pp. 183–189, 1988.

(List continued on next page.)

*Primary Examiner*—John J. Wilson
*Attorney, Agent, or Firm*—Jenkens & Gilchrist

[57] ABSTRACT

A two-piece healing abutment for forming an aperture in gingiva overlying an artificial root means installed in a jawbone of a patient's mouth is set forth. The root means has an upper end that is to be exposed in the aperture. The two-piece healing abutment comprises a first component and a second component. The first component has a transmucosal portion with an exterior surface for defining the aperture in the gingiva. The first component also has an internal bore extending therethrough and a lower end for engaging the upper end of the root means. The second component attached the first component on the root means. The second component extending through the bore of the first component and engaging the root means.

72 Claims, 2 Drawing Sheets

U.S. PATENT DOCUMENTS

| | | | |
|---|---|---|---|
| 5,015,186 | 5/1991 | Detsch | 433/173 |
| 5,030,096 | 7/1991 | Hurson et al. | 433/173 |
| 5,035,619 | 7/1991 | Daftary | 433/173 |
| 5,040,983 | 8/1991 | Binon . | |
| 5,071,351 | 12/1991 | Green, Jr. et al. . | |
| 5,073,111 | 12/1991 | Daftary | 433/173 |
| 5,100,323 | 3/1992 | Friedman et al. . | |
| 5,106,300 | 4/1992 | Voitik | 433/173 |
| 5,135,395 | 8/1992 | Marlin | 433/174 |
| 5,145,371 | 9/1992 | Jorneus . | |
| 5,145,372 | 9/1992 | Daftary et al. | 433/173 |
| 5,188,800 | 2/1993 | Green, Jr. et al. . | |
| 5,209,659 | 5/1993 | Friedman et al. . | |
| 5,209,666 | 5/1993 | Balfour et al. . | |
| 5,213,502 | 5/1993 | Daftary | 433/172 |
| 5,281,140 | 1/1994 | Niznick | 433/172 |
| 5,292,252 | 3/1994 | Nickerson et al. | 433/173 |
| 5,297,963 | 3/1994 | Daftary | 433/172 |
| 5,334,024 | 8/1994 | Niznick | 433/173 |
| 5,336,090 | 8/1994 | Wilson, Jr. et al. | 433/172 |
| 5,338,196 | 8/1994 | Beaty et al. | 433/172 |
| 5,431,567 | 7/1995 | Daftary | 433/173 |
| 5,433,606 | 7/1995 | Niznick et al. | 433/173 |
| 5,547,377 | 8/1996 | Daftary | 433/173 |
| 5,564,921 | 10/1996 | Marlin | 433/172 |

OTHER PUBLICATIONS

Perri DDS, George et al., *Single Tooth Implants*, CDA Journal, vol. 17, No. 3, Mar. 1989.

DIA™ Dental Imaging Associates, Implanted—The Source, "The Anatomical Abutment System", Copyright Date Oct. 9, 1991 on p. 10. (Front Cover, pp. 1–10 and Back Cover).

Steri–Oss®, Product Catalog, Feb. 1992, Cover Page, pp. 7, 14, and Last Page.

Branemark System (Nobelpharma), Product Catalog Prosthetics, 1991, 24 pages.

Steri–Oss®, Product Catalog, Sep. 1990, 36 pages.

IMTEC Hexed–Head™ Implant System, Spring 1993 Catalog, 15 pages.

Interpore International, IMZ™ Prosthetic Flow Chart, Jul. 1993, 2 sheets.

Impla–Med, Catalog, Mar. 1991, 16 pages.

Stryker Dental Implants, Catalog Data Sheets, Undated, 4 sheets.

Stryker Dental Implants, Price List, Jun. 1, 1993, 46 pages.

Oratronics, Inc., "Options for Oral Implantology . . . Oratronics Endosseous Tri–Dimensional T–3D Oral Implant Healing System (OIHS)", 1978 8 pages.

TWO-PIECE HEALING ABUTMENT SYSTEM

This application is a divisional application of Ser. No. 08/527,508, filed Sep. 13, 1995, now U.S. Pat. No. 5,674,071 which is a file wrapper continuation of Ser. No. 08/248,497, filed May 24, 1994, now abandoned, which is a continuation of Ser. No. 08/043,928, filed Apr. 8, 1993, now U.S. Pat. No. 5,338,196.

BACKGROUND OF THE INVENTION

The field of restorative dentistry using artificial roots in the presently preferred form of osseointegrated cylinder shaped dental implants has progressed to the level where attention is now being given to providing restorations on them that closely replicate natural dentition in appearance, especially where the teeth emerge from the gums. The problems of achieving a natural looking emergence profile are addressed using a technique for fabricating implant supported restorations directly to an implant, employing custom wax patterns fashioned on abutment cylinders to achieve, for example, a custom made porcelain fused to metal restoration. This technique is described in published articles that appeared in The International Journal of Oral & Maxillofacial Implants, Vol. 3, Number 1, 1988 at pages 25–26 "Single Tooth implant Supported Restorations" Lewis, S. G. et al., and Number 3, 1988 at pages 183–189 "The 'UCLA' Abutment", Lewis, S. G. et al. A similar result using a different abutment is described in U.S. Pat. No. 4,988,298, which is owned by the Assignee of the present invention. The problem is incompletely addressed in U.S. Pat. No. 5,073,111 issued to Daftary Dec. 17, 1991.

The dental restoration of a wholly or partially edentulous patient with dentition supported on dental implants is now frequently done in two stages. In the first stage the implant is placed and left to integrate with the jawbone. The second stage begins with re-accessing the implant through the gum and maintaining access with a healing cap or the like, and continues through the fabrication of restorative dentition in the laboratory using measurements and other information taken from time to time from the patient. During that time the patient may have only a healing cap in his or her mouth, or according to more recent and sophisticated procedures the patient may be fitted with temporary dentition from which additional refining measurements can be taken. Nevertheless, the healing abutments and the transfer copings, or pick up copings, of the prior art do not cooperate to provide room for making and installing on the implant an artificial tooth having an aesthetically pleasing or anatomically correct emergence profile. The gingival aspect of an implant is, typically not more than about 4.1 mm in diameter, whereas the longer (mesial-distal) dimension of a natural tooth where it emerges from the gum is between about 4.5 mm and about 8.0 mm. According to present practice, healing abutments, which are cylindrical in cross section, are chosen to approximate the mesial-distal dimension of the tooth being replaced. At the same time, the transfer copings, or pick up copings, of the prior art are all one size, about 4.5 mm in diameter. As a result, a gap is left in the gingiva, around the coping, and impression material fills this gap when an impression is taken. The gingiva also tend to collapse into this gap, resulting in less than accurate replication of the conditions in the patient's mouth. As a further consequence of these problems, it is difficult to make soft tissue models accurately. Stone models replicate these errors, and this requires technicians to shape the stone manually to comply with the conditions in the patient's mouth, or risk producing a crown with an inaccurate emergence profile or crown to abutment margin that is misplaced. These are severe problems, resulting from the fact that the designers of prior art components have thus far failed to recognize them. The present invention teaches new surgical and laboratory components, and new procedures, which eliminate such inaccurate and time wasting procedures, and improve the art of making anatomically correct and aesthetically pleasing dental restoration.

GENERAL NATURE OF THE INVENTION

In accordance with the present invention, a healing cap or healing abutment sized to maintain space for a desired emergence profile through the gum is used at the beginning of the second stage, in combination with an impression coping, or a pick up coping, having similar size specifications so that when the impression coping is fitted to the implant for taking the impression from which the stone model will be made the space for the desired emergence profile established in the gum by the healing abutment, or cap, will be preserved and replicated in the stone model, and in a soft tissue model, if desired. From such models restorative dentition can be fabricated without requiring the use of a specially contoured tooth support abutment as taught by Daftary, for example. Rather, artificial teeth replicating in all material respects the natural teeth that they replace can be fashioned on the model using components that have become standard in the art.

In one of its aspects the invention teaches a new method of preparing an aesthetically pleasing, as well as anatomically correct dental restoration on a natural or artificial root comprising first the step of preparing in the gingiva overlying the root an opening to the gingival aspect of the root, which opening is sufficient to accommodate the shape and contour of a natural tooth emerging through the gingiva from the root, followed by the step of making a rigid (e.g., stone) model that reproduces in stone or in overlying soft tissue exactly that opening and gingival aspect of the root, and then the step of forming on the model an artificial tooth that replicates in that opening the shape, size and contours desired in the restoration, and finally installing that restoration on the root. In another aspect, the invention provides a healing member (sometimes called a cap) that has a transmucosal section having at one end the subgingival cross sectional size and shape of the artificial root and where it emerges from the gingiva the mesial-distal size of the natural tooth being replaced, and means to attach that healing member non-rotatively to the root, for establishing the above mentioned opening in the gingiva. In another aspect, the invention provides a transfer coping for use in making the above mentioned rigid model having a transmucosal section that is substantially identical in cross sectioned size and shape to the transmucosal section of the healing member so as to fit fully within the opening in the gingiva that was formed by the healing member, and a supragingival section shaped for non-rotational embedment in resilient modelling material, together with means to attach the coping non-rotatively to the root. In still another aspect, the invention provides sets of matched pairs of healing members and transfer copings shaped and sized for use according to the invention to prepare restorations of particular types of teeth, such as molars, premolars, bicuspids, and incisors, as examples.

These and other features of the invention will be explained in greater detail in the following description of certain exemplary embodiments of the invention referring to the accompanying drawings in which.

DETAILED DESCRIPTION OF THE DRAWINGS

Figure 1:
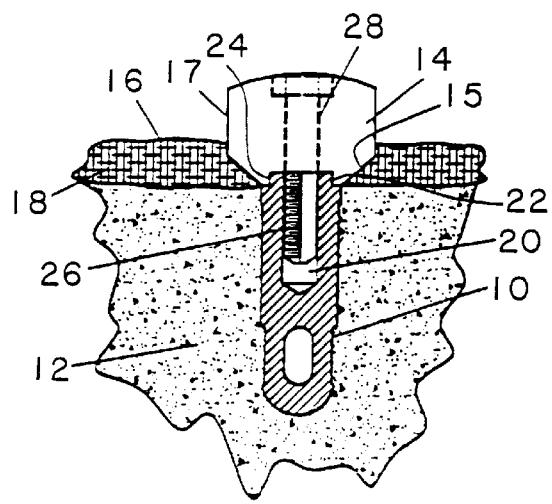
FIG. 1 is a longitudinal section that shows an implant installed in a bone with a healing cap in place.

FIG. 1 schematically illustrates a dental implant 10, of the osseointegrated type installed in a section of jawbone 12. The "second stage surgery" has begun, and a healing abutment 14 is in place on the implant. In order to provide for a more natural emergence profile in the final restoration, this abutment expands in a tapered transmucosal section 15 from the end contacting the implant toward an outer surface 16 of surrounding gingiva 18, beyond which walls 17 of the abutment extend vertically. As shown in FIG. 1, a portion of the vertical walls 17 is immersed in the gum tissue, below the outer surface 16, together with the tapered section 15. The implant has an internally threaded bore 20 axially located in it, surrounded at its gingival opening by a non-round boss 22, the external cross section of which typically is hexagonal. The healing abutment 14 has a corresponding non-round socket 24 enveloping the boss 22. In the illustrated embodiment through-bolt 26 passing through an axial bore 28 in the healing abutment is used to attach the abutment to the implant, in a well known manner. Attached in this manner, the healing abutment is not able to be rotated around the axis of the bolt. Healing abutments according to the invention may be prefabricated with a transmucosal section 15 having at the gingival surface 16 a round cross sectional shape the diameter of which is approximately equal to the mesial-distal dimension of the lost tooth being restored. Alternatively, the peripheral contour in the tapered section 15 may closely replicate the emergence profile of the natural tooth that was in the site where the implant 10 is installed. The invention contemplates providing sets of such prefabricated healing abutments, together with matching impression copings. The supragingival vertical walls of the healing abutment and the impression copings used with it may also be contoured to mimic the natural tooth cross-section, depending on the thickness of the gingiva 18 and the corresponding vertical dimension of the abutment.

Figure 2:
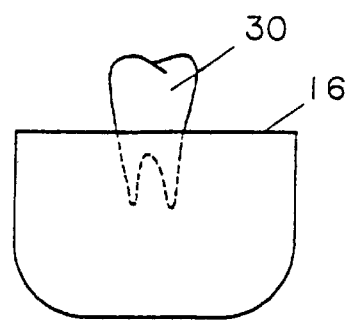
FIG. 2 shows a natural bicuspid.

FIG. 2 shows the general contours of a bicuspid 30 emerging from the outer surface 16 of the gingiva. A typical bicuspid is approximately 5.5 mm in mesial-distal dimension at the surface 16. A typical standard abutment or impression coping is at most 4.5 mm in diameter. Some teeth, e.g., molars, may be as much as 6.0 or 7.0 mm in mesial-distal dimension. Moreover, as appears in FIG. 6, which illustrates the cross section of an emergence profile 75 characteristic of an anterior tooth (not shown), it is also desirable to be able to provide for emergence profiles the cross sections of which do not even approximate round. To address these problems the invention provides methods and means to create and preserve openings in the gingiva 18 that are significantly larger than the cross section of the implant 10 and that may be round, or may have any desirable shape, and to preserve each such opening throughout the laboratory procedure for making and fitting the relevant dental restoration. Thus, as has been mentioned, the cross sectional shape of the transmucosal tapered portion 15 and the vertical wall portion 17 of the healing abutment may be round as long as its diameter approximates the mesial-distal size of the natural tooth.

Figure 3:
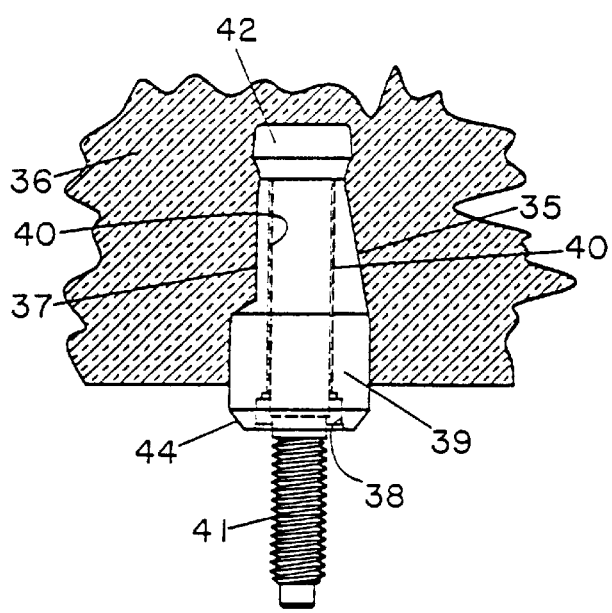
FIG. 3 is a longitudinal section that shows a transfer coping used to make an impression.

FIG. 3 shows a transfer coping 35 of a kind used to take impressions, buried in an impression material 36. The essential structure of this impression coping is described and claimed in U.S. Pat. No. 4,955,811, which is owned by the Assignee of the present invention. This impression coping has a flat surface 37 for locating it non-rotationally in the impression material, a hexagonal socket 38 in its base 39 for fixing it non-rotationally on the implant 10, an axial through bore 40 and a bolt 41 with an expanded head 42 for holding it in the impression material. The bolt 41 is used to attach the impression coping 35 to the implant 10. For the purposes of the present invention, the impression coping has a tapered section 44 at its end surrounding the socket 38 that replicates in size and shape the tapered transmucosal section 15 of the healing abutment 14. As shown in FIG. 3, a portion of the base 39 emerges from the impression material 36, together with the tapered section 44. The base 39 may also be contoured to mimic the natural cross section of the tooth being replaced, as its mentioned above.

Figure 4:
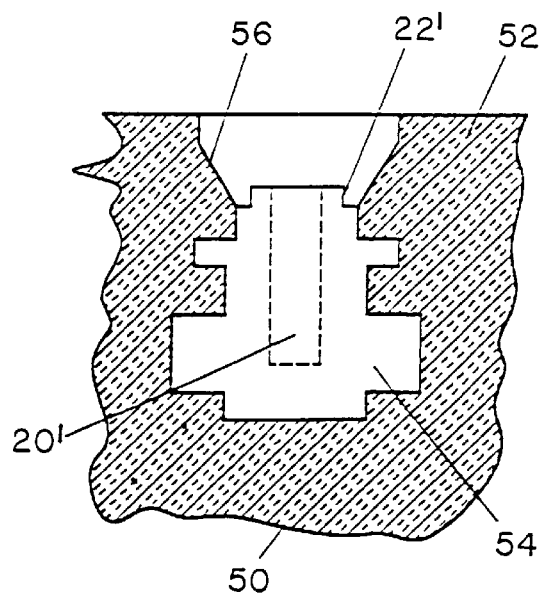
FIG. 4 is a longitudinal section that shows a stone model made from the impression.

FIG. 4 is a stone model 50 of the patient's implant installation site shown in FIG. 1. An implant replica 54 is encased in stone 52. according to well known dental laboratory practice. The replica 54 has a threaded bore 20' and a non-round boss 22' that are identical to the bore 20 and boss 22 of the implant 10. A tapered recess 56 in the surface of the stone surrounding the end of the replica 54 matches in size and shape the tapered section 44 and a part of the base 39 of the impression coping 35. Thus, the healing abutment fits equal!y well on the implant replica as on the implant.

The illustration in FIGS. 1,3, and 4 of a process in which the openings in the gingiva 18 and the model SC have a "vertical" portion as well as the tapered portion is exemplary only, and is not intended to limit the invention to that feature.

Figure 5:
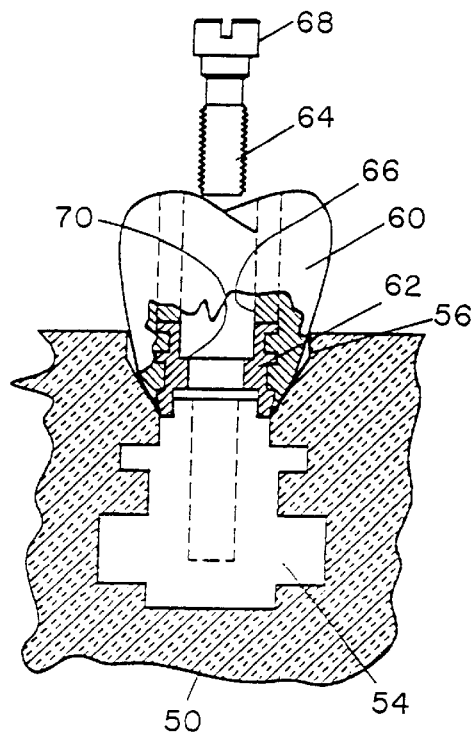
FIG. 5 shows the invention as used to replicate the natural tooth of FIG. 2.

An artificial bicuspid 60, as shown in FIG. 5, can be made with the aid of the model 50. A known form of core 62 is non-rotatively attachable to the implant replica with a screw bolt 64, passed through a through-bore 66 in the core. Head 68 of the bolt comes to rest on a shoulder 70 in the core 62, holding the core firmly attached to the implant replica 54 within the tapered recess 56. The artificial tooth is fashioned on the core using any available dental material, such as porcelain or acrylic, for example. The dental material extends well within the tapered recess 56, so that outside this recess the core material cannot be seen. The core itself can be made of any suitable rigid material, such as titanium and its dilute alloys. After being fashioned and anatomically shaped as desired, the artificial tooth 60 can be transferred to the implant 10 and its appearance will be as is shown in FIG. 2. It will emerge from the gingiva 18 looking exactly the same as a natural tooth. According to well known dental practice, the opening into the core at the top of the tooth 60 will be filled with a suitable dental cement or the like, and polished so as to be for all practical purposes not distinguishable from the rest of the tooth. The above mentioned U.S. Pat. No. 4,988,298 illustrates an, artificial tooth that can benefit from the invention.

Figure 6:
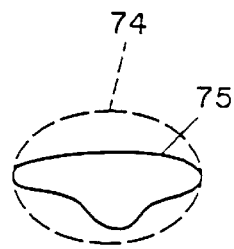
FIG. 6 shows the cross section of a natural emergence profile that the invention can replicate.

Because the component parts used in this invention can be made so that they are non-rotatably attachable together, it is not necessary that they be cylindrical in cross section where they are attachable one to the other. Thus, the healing abutment 14, the base 39 of the impression coping 35, and the subgingival section of the artificial tooth 60 can each be given the same cross sectional size and shape, changing gradually from round at the subgingival aspect of the implant fixture 10 to non-round proceeding toward the gingival surface through which the artificial tooth will emerge from the surface 16 of the overlying gingiva. In this manner that size and shape can initially be established by the healing abutment in the opening through the gingiva 18, and the same size and shape in the correct orientation around the axis of the implant 10 can be replicated and preserved in the model 50, thereby enabling the tooth 60 to be formed in the laboratory with the correct emergence profile. This feature of the invention is particularly advantageous when restoring anterior dentition, where the emergence cross section, e.g., 75 as is indicated in FIG. 6, has segments that are almost straight, and curved segments that turn on short radii.

The invention is not limited to the use of non-rotatively attachable components. In its more general aspects, the invention contemplates providing transmucosal openings that may be round with a diameter that approximates the mesial-distal dimension of the missing tooth that is being replaced, and preserving that dimension in a round opening throughout the laboratory procedure. This simple arrangement provides the basic advantages of the invention, which include eliminating the need to surgically expand a trans-tissue opening that was originally, or has become, too small to receive the restoration, and eliminating the need for laboratory technicians to hand finish stone models in which the trans-tissue opening was incorrectly formed due to causes that are mentioned above. Provided the trans-tissue opening is formed and maintained large enough to receive the restoration, last minute surgery is not needed, and the tissue will grow to the restoration. Referring to FIG. 6, dashed line circle 74 represents a trans-tissue opening that is larger then the tooth 75. In this situation, there is no need to provide the non-rotative features such as the mating non-round boss 22 and socket 24.

According to the invention, hearing abutments 14 and transfer copings 35 may be prefabricated in sets of pairs, each pair having an "emergence profile contour" that is representative of a range of teeth of a particular type; that is, for example, large molars, small molars, premolars, bicuspids, and anterior incisors. The restorative dentist may then choose a pair that most closely replicates the emergence profile that is desired, modify the members of that pair if such is deemed necessary or desirable, and then make a restoration in accordance with the present invention that will be aesthetically pleasing and very close to anatomically correct.

Figure 7:
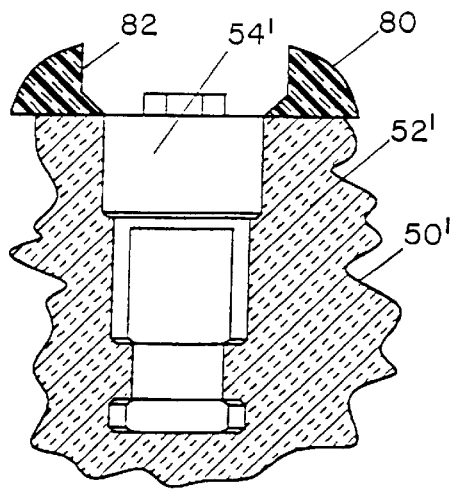
FIG. 7 is a cross section that shows a soft tissue model.

FIG. 7 shows a stone model 50' similar to the model 50 of FIG. 4, but in cross section rather than in longitudinal section, and including a stone foundation 52' rigidly holding an implant replica 54'. A soft tissue layer 80, which replicates the human gingiva 18, overlies the stone part. This layer can be made of any suitable plastics or rubber-like material having physical properties such as softness and elasticity that resemble the physical properties of human gum tissue. Certain silicone based rubber and plastics materials are suitable, preference being given to those that can be fabricated from a soft flowable state. In use, the soft flowable plastics material is placed in the impression around the tapered section 44 and emerging portion of the base 39 of the transfer coping 35 to a thickness the same as that of the patient's gingiva 18. The resulting opening 82 is similar to the opening 56 in the stone that is shown in FIG. 4. It has the advantage that the laboratory technician can manipulate the model exactly as the dentist manipulates the patient's gingiva.

Figure 8:
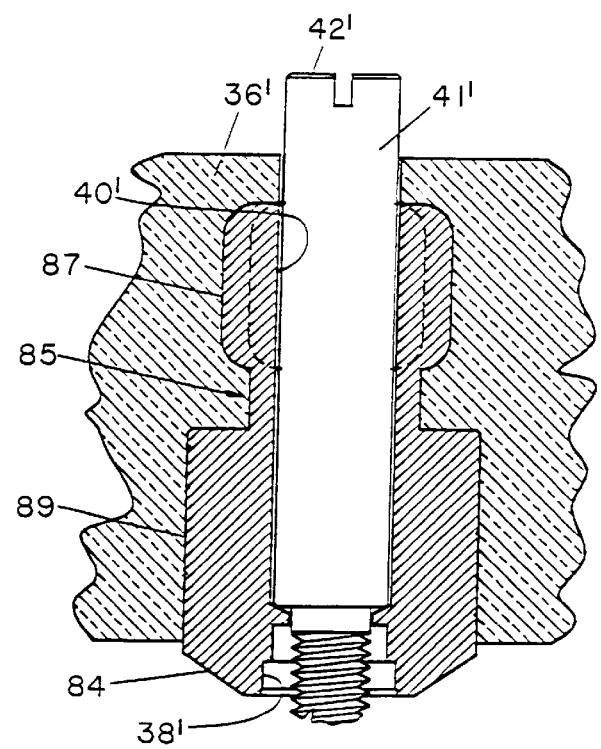
FIG. 8 shows a pick up coping used to make an impression.

FIG. 8 shows a pick-up coping 85 buried in, an impression material 36'. This impression coping has a non-round head portion 87 for anchoring the coping non-rotationally on the implant, if desired, an axial through bore 40' and a bolt 41' passing through this bore to attach the impression coping to the implant. The proximal end 42' of the bolt has no expanded head on it for the reason that in use when an impression is taken, this end of the bolt extends through a hole in the impression tray (not shown) and, when the impression material has set up in the tray the bolt 41' is unscrewed from the implant by accessing its proximal end 42' from the outside, the tray and the coping 85 remains in (is "picked up" by) the impression material, being anchored therein by its expanded head 87. For the purposes of this invention, the pick up coping 85 functions like the transfer coping 35 of FIG. 3. Thus, the base 89 is expanded to a diameter that approximates the mesial-distal dimension of the natural tooth that is being restored and tapered section 84 reduces subgingival!y to the diameter of the implant or other underlying support that may be present. Like the base 39 in FIG. 3, the base 89 may be contoured to mimic the cross section of the natural tooth.

What is claimed is:

1. A healing abutment for attachment to a dental implant installed in a jawbone having overlying gingiva, said dent implant having an upper end, said healing abutment comprising:

a body having a transmucosal portion with an exterior surface for forming an aperture through said gingiva, said body having an internal bore extending therethrough and a lower end for engaging said upper end of said dental implant, said body further having an upper surface above said transmucosal portion; and a screw for attaching said body to said dental implant, said screw extending through said bore of said body and engaging said dental implant, said screw including a top portion that, together with said upper surface, forms an exposed uppermost region of said healing abutment.

2. The healing abutment of claim 1 wherein said transmucosal portion has a transverse cross-section that increases in area in a direction away from said lower end.

3. The healing abutment of claim 1 wherein said upper end of said dental implant and said lower end of said body form cooperating anti-rotational surfaces.

4. The healing abutment of claim 3 wherein said transmucosal portion has a transverse cross-section that increases in area in a direction away from said lower end.

5. The healing abutment of claim 1 wherein said transmucosal portion includes a generally conical lower region and a generally cylindrical upper region.

6. The healing abutment of claim 1 wherein said transmucosal portion is tapered and has a smaller section adjacent to and generally the size and shape of said upper end of said dental implant and a larger section having a transverse dimension generally replicating the width of a natural tooth where the natural tooth emerged from the gingiva.

7. The healing abutment of claim 6 wherein said smaller section is substantially round and said larger section is non-round.

8. The healing abutment of claim 7 wherein said smaller section gradually changes from round to the non-round shape of said larger section.

9. The healing abutment of claim 1 wherein said internal bore of said body includes a shoulder for engaging said screw to axially retain said body on said dental implant.

10. The healing abutment of claim 1, wherein said top portion of said screw does not protrude above said upper surface of said body.

11. A healing abutment for attachment to a dental implant installed in a jawbone having overlying gingiva, said dental implant having an upper end, said healing abutment comprising:

a body having a transmucosal portion with an exterior surface for forming an aperture in said gingiva, said body having an internal bore extending therethrough and a lower end for engaging said upper end of said dental implant, said transmucosal portion including regions with non-round cross-sections; and a screw for attaching said body to said dental implant, said screw extending through said bore of said body and engaging said dental implant.

12. The healing abutment of claim 11 wherein said upper end of said dental implant and said lower end of said body form cooperating anti-rotational surfaces.

13. The healing abutment of claim 11 wherein said transmucosal portion has a transverse cross-section that generally replicates the emergence profile of a natural tooth.

14. The healing abutment of claim 11 wherein said transmucosal portion is tapered and has a smaller section adjacent to and generally the size and shape of said upper end of said dental implant and a larger section having a transverse dimension generally replicating the width of a natural tooth where the natural tooth emerged from the gingiva.

15. The healing abutment of claim 11 wherein said internal bore of said body includes a shoulder for engaging a portion of said screw to axially retain said body on said dental implant.

16. The healing abutment of claim 11, wherein said screw includes an upper portion that forms at least a portion of an exposed uppermost region of the combination of said body and said screw.

17. A kit of healing components each of which is useful for forming an aperture in gingiva overlying an artificial dental implant installed in a jawbone of a patient's mouth, said dental implant having an upper end to be exposed in said aperture, said kit of healing components comprising:

a plurality of bodies each having a transmucosal portion with an exterior surface for defining said aperture in said gingiva, each of said plurality of bodies having an internal bore extending therethrough, a lower end for engaging said upper end of said dental implant, and an upper surface above said transmucosal portion, said transmucosal portion of at least one of said plurality of bodies having a different transverse dimension than remaining ones of said plurality of bodies; and at least one screw adapted to attach one of said plurality of bodies to said dental implant, said screw extending through said bore of said body and engaging said dental implant, said screw including a top portion that, together with said upper surface, forms an exposed uppermost region of a combination of said one of said plurality of bodies and said screw.

18. The kit of healing components of claim 17, wherein said transmucosal portion of each of said plurality of bodies generally replicates the emergence profile of a natural tooth.

19. The kit of healing components of claim 17, wherein said one of said plurality of bodies with said different transverse dimension has substantially the same shape in its transmucosal portion as one of said remaining ones of said plurality of bodies.

20. The kit of healing components of claim 17, wherein said transmucosal portion of at least one said plurality of bodies is non-round.

21. The kit of healing components of claim 20, wherein said transmucosal portion of at least another of said plurality of bodies is substantially round.

22. The kit of healing components of claim 17, wherein said top portion of said screw does not protrude above said upper surface of said one of said plurality of bodies.

23. The kit of healing components of claim 17, wherein said at least one screw is capable of attaching each one of said plurality of bodies to said dental implant.

24. The kit of healing components of claim 17, wherein said one of said plurality of bodies with said different transverse dimension has substantially a different shape than said remaining ones of said plurality of bodies.

25. A healing abutment for attachment to a dental implant installed in a jawbone and having overlying gingiva, said dental implant having an upper end, said healing abutment comprising:

a body having a transmucosal portion with an exterior surface for forming an aperture in said gingiva, said body having an internal bore extending therethrough that includes a shoulder, said body having a lower end for engaging said upper end of said dental implant, said transmucosal portion including a region with a non-round cross-section that generally replicates the emergence profile of a natural tooth, said lower end being substantially the same size and shape as said upper end of said dental implant and including a non-round fitting for mating with a correspondingly shaped fitting of said dental implant for effecting anti-rotational engagement therewith; and a screw for axially retaining said body on said dental implant including a threaded lower stem, said screw extending through said bore of said body so that a portion of said screw engages said shoulder while said threaded lower stem engages an internally threaded bore in said dental implant, said screw including a top portion that forms at least a portion of an exposed supragingival region of said healing abutment.

26. A healing abutment for attachment to a dental implant installed in a jawbone having overlying gingiva, said dental implant having an upper end, said healing abutment comprising:

a body having a transmucosal portion with an exterior surface for forming an aperture in said gingiva, said body having an internal bore extending therethrough, said body further including a shoulder and a lower end for engaging said upper end of said dental implant, said transmucosal portion including a region with a round cross-section that has a transverse dimension that generally replicates a transverse dimension of a natural tooth to be replaced, said lower end being substantially the same size and shape as said upper end of said dental implant and including a non-round fitting for mating with a correspondingly shaped fitting of said dental implant for effecting anti-rotational engagement therewith; and a screw for axially retaining said body on said dental implant including a threaded lower stem, said screw extending through said bore of said body so that a portion of said screw engages said shoulder while said threaded lower stem engages an internally threaded bore in said dental implant, said screw including a top portion that forms at least a portion of an exposed supragingival region of said healing abutment.

27. The healing abutment of claim 26 wherein said top portion of said screw does not protrude above said upper surface of said body.

28. A method of forming gingiva adjacent to an artificial dental implant into a particular shape to create an aperture leading to an upper end of said dental implant, said method comprising the steps of exposing said upper end of said dental implant;

placing a first healing component onto said upper end of said dental implant, said first healing component having a transmucosal portion which has an exterior surface for defining said particular shape of said aperture;

retaining said first healing component on said dental implant with a second healing component that engages said first healing component and that, together with said first healing component forms an exposed uppermost region of a combination of said first and second healing components; and allowing said gingiva to heal around said first healing component.

29. The method of claim 28, wherein said step of placing said first healing component onto said upper end of said dental implant includes the step of mating non-rotational fittings on said first healing component and said dental implant.

30. The method of claim 28, wherein said step of retaining said first healing component on said dental implant includes the step of inserting said second component through a bore in said first healing component.

31. The method of claim 30, wherein said step of retaining said first healing component on said dental implant includes the step of threadably engaging a lower stem of said second component with an internally threaded bore in said dental implant.

32. The method of claim 28, wherein said particular shape is non-round.

33. A kit of transfer-type impression copings for use in making a model of a site in a mouth of a patient, said site containing a dental implant in a jawbone and an opening in gingiva overlying said jawbone, said transfer-type impression coping remaining on said dental implant after resilient impression material is removed from said site, each of said transfer-type impression copings in said kit comprising:

a transmucosal section with a non-round shape;

a supragingival section adapted for embedment in said resilient impression material; means for attaching said transfer coping to said dental implant; and wherein said non-round shape of a first transfer-type coping closely replicates a transmucosal section of a typical molar and said non-round shape of a second transfer-type coping closely replicates a transmucosal section of a typical incisor.

34. The kit of transfer-type copings according to claim 33 further including a third transfer-type coping with said non-round shape closely replicating a transmucosal section of a typical bicupsid.

35. The kit of transfer-type copings according to claim 33 further including a third transfer-type coping with said non-round shape closely replicating a transmucosal section of a typical premolar.

36. The kit of transfer-type copings according to claim 33 wherein said attaching means is a screw that is inserted through a bore in said transfer-type coping and that engages a threaded hole in said dental implant.

37. The kit of transfer-type copings according to claim 33 wherein the cross-section at an end surface adjacent to said transmucosal section is substantially round and changes gradually to non-round proceeding away from said end surface.

38. The kit of transfer-type copings according to claim 33 wherein said transmucosal section includes exterior walls which are nearly parallel to a central axis of said transfer-type coping.

39. A kit of pick-up type impression copings for use in making a model of a site in a mouth of a patient, said site containing a dental implant in a jawbone and an opening in gingiva overlying said jawbone, said pick-up coping and resilient impression material being simultaneously removed from said site after an impression is taken, each of said pick-up copings in said kit comprising:

a transmucosal section with a non-round shape;

a supragingival section adapted for embedment in said resilient impression material including means for being retained within said resilient impression material;

means for attaching said pick-up coping to said dental implant; and wherein said non-round shape of a first pick-up coping closely replicates a transmucosal section of a typical molar and said non-round shape of a second pick-up coping closely replicates a transmucosal section of a typical incisor.

40. The kit of pick-up copings according to claim 39 further including a third pick-up coping with said non-round shape closely replicating a transmucosal section of a typical bicupsid.

41. The kit of pick-up copings according to claim 39 further including a third pick-up coping with said non-round shape closely replicating a transmucosal section of a typical premolar.

42. The kit of pick-up copings according to claim 39 wherein said attaching means is a screw that is inserted through a bore in said pick-up coping and that engages a threaded hole in said dental implant.

43. The kit of pick-up copings according to claim 39 wherein the cross-section at an end surface adjacent to said transmucosal section is substantially round and changes gradually to non-round proceeding away from said end surface.

44. The kit of pick-up copings according to claim 39 wherein said transmucosal section includes exterior walls which are nearly parallel to a central axis of said pick-up coping.

45. A kit of healing components each of which is useful for forming an aperture in gingiva, said kit of healing components being adapted for fixation on a dental implant located in a jawbone, each of said healing components in said kit comprising:

a non-round transmucosal section to form a corresponding non-round shape of said aperture, said transmucosal section of at least one healing component being a different shape than the remaining ones of said healing components;

an end surface adjacent to said transmucosal section for contacting said dental implant; and means to attach said healing component to said dental implant.

46. The kit of healing components according to claim 45 wherein the cross-section at said end surface is substantially round and changes gradually to non-round proceeding away from said end surface.

47. The kit of healing components according to claim 45 wherein said transmucosal section includes exterior walls which are nearly parallel to a central axis of said healing component.

48. The kit of healing components according to claim 45 wherein said non-round shape of a first healing component closely replicates a transmucosal section of a typical molar and said non-round shape of a second healing component closely replicates a transmucosal section of a typical incisor.

49. The kit of healing components according to claim 48 further including a third healing component having a non-round shape closely replicating a transmucosal section of a typical bicupsid.

50. The kit of healing components according to claim 48 further including a third healing component having a non-round shape closely replicating a transmucosal section of a typical premolar.

51. The kit of healing components according to claim 45 wherein said attaching means is a screw that is inserted through a bore in said healing component and that engages a threaded hole in said dental implant.

52. A kit of components for use in making an artificial tooth which emulates a natural tooth in a mouth of a patient, said mouth including a site containing a dental implant in the jawbone and an aperture in gingiva overlying said jawbone, said kit comprising:
a plurality of healing components each having a first transmucosal section with a non-round shape to form a corresponding non-round shape of said aperture and an end surface adjacent to said first transmucosal section for contacting said dental implant;
first means to attach one of said plurality of healing components to said dental implant;
a plurality of impression copings each having a second transmucosal section with a non-round shape and a supragingival section adapted for embedment in resilient impression material;
second means to attach one of said plurality of impression copings to said dental implant within said aperture; and
wherein said non-round shapes of a first healing component and a first impression coping in said site closely replicate a transmucosal section of a typical molar, and said non-round shapes of a second healing component and a second impression coping closely replicate a transmucosal section of a typical incisor.

53. The kit of components according to claim 52 further including a third healing component and a third impression component each having non-round shapes closely replicating a transmucosal section of a typical bicupsid.

54. The kit of components according to claim 52 further including a third healing component and a third impression component each having non-round shapes closely replicating a transmucosal section of a typical premolar.

55. The kit of components according to claim 52 wherein said healing components and said impression components each have a non-rotational fitting to mate with said dental implant.

56. The kit of components according to claim 52 wherein at least one of said impression components is a transfer-type coping.

57. The kit of components according to claim 52 wherein at least one of said impression components is a pick-up coping.

58. The kit of components according to claim 52 wherein the cross-section at said end surface of said healing component is substantially round and changes gradually to non-round proceeding away from said end surface of said healing component, and the cross section at a bottom surface of said impression coping is substantially round and changes gradually to non-round proceeding away from said bottom surface of said impression coping.

59. The kit of components according to claim 52 wherein each of said first and second transmucosal sections includes exterior walls which are nearly parallel to a central axis of said healing component and said impression coping, respectively.

60. A healing abutment to be attached to an implant having an internally threaded bore, said implant being installed in living jawbone which has overlying gingiva, said healing abutment comprising:
a member having a lower surface for engaging said implant and an exterior wall for engaging and forming an aperture through said overlying gingiva, said member having a bore extending therethrough, said member has a non-round cross-section: and
a screw for extending through said bore and having a threaded stem for engaging said threaded bore of said implant, said screw having a head which does not protrude above said upper surface of said member.

61. The healing abutment of claim 60, wherein said head of said screw forms an exposed uppermost region of said healing abutment.

62. A healing abutment for forming an aperture in gingiva overlying an artificial root means installed in a jawbone of a patient's mouth, said root means having an upper end to be exposed in said aperture, said healing abutment comprising:
a first component having a transmucosal portion with an exterior surface for defining said aperture in said gingiva, said first component having an internal bore extending therethrough and a lower end for engaging said upper end of said root means, said first component further having an upper surface above said transmucosal portion, said transmucosal portion includes a generally conical lower region and a generally cylindrical upper region; and
a second component for attaching said first component to said root means, said second component extending through said bore of said first component and engaging said root means, said second component forming at least a portion of an exposed uppermost region of said healing abutment.

63. The healing abutment of claim 62, wherein said second component does not protrude above said upper surface of said body.

64. A healing abutment for use with an implant that is installed in a jawbone having overlying gingiva, said healing abutment comprising:
a member with an external side surface for forming an aperture in said overlying gingiva and an internal surface defining a bore extending through said member, said external surface terminating in an upper surface that forms a first part of an exposed uppermost region of said healing abutment, said member has a non-round cross-section; and
a screw extending through said bore and holding said member on said implant, said screw having a threaded stem for threadably engaging a threaded bore of said implant and a head that forms a second part of an exposed uppermost region of said healing abutment.

65. The healing abutment of claim 64, wherein said internal surface further defines a shoulder for engaging a head of said screw.

66. The healing abutment of claim 65, wherein said shoulder is generally perpendicular to a central axis of said member extending through said bore.

67. The healing abutment of claim 64, wherein said external side surface includes a generally conical lower region and a generally cylindrical upper region.

68. The healing abutment of claim 64, wherein said head of said screw does not protrude above said upper surface of said body.

69. An impression coping to be attached to a dental implant installed in a jawbone and for use with resilient impression material, said impression coping comprising:

a transmucosal section with a non-round shape;

a supragingival section adjacent to said transmucosal section adapted for embedment in said resilient impression material; and a screw portion for threadably engaging a threaded bore of said implant to secure said impression coping to said dental implant.

70. The impression coping of claim 69 wherein said impression coping includes an internal surface defining a bore and said screw portion is a separate component extending through said bore.

71. The impression coping of claim 70, wherein said supragingival section has a portion with a non-round cross-section to provide indexing of said impression coping in said material.

72. A method of forming gingiva adjacent to an artificial dental implant into a particular non-round shape to create an aperture leading to an upper end of said dental implant, said method comprising the steps of:

exposing said upper end of said dental implant;

placing a first healing component onto said upper end of said dental implant, said first healing component having a transmucosal portion which has an exterior surface for defining said particular non-round shape of said aperture;

retaining said first healing component on said dental implant with a second healing component that engages said body; and allowing said gingiva to heal around said first healing component with only said first and second healing components attached to said dental implant.

\* \* \* \* \*

UNITED STATES PATENT AND TRADEMARK OFFICE
CERTIFICATE OF CORRECTION

PATENT NO. : 6,129,548
DATED : October 10, 2000
INVENTOR(S) : Lazzara et al.

It is certified that error appears in the above-identified patent and that said Letters Patent is hereby corrected as shown below:

<u>Title page 2, Item [56], U. S. Patent Documents, add the following references</u>

| | | | |
|---|---|---|---|
| 5,662,476 | 9/1997 | Ingber et al. | 433/213 |
| 5,674,073 | 10/1997 | Ingber et al. | 433/213 |

<u>Column 6, claim 1,</u>
Line 29, delete "dent" and insert -- dental --

<u>Column 9, claim 28,</u>
Line 13, after "component" add -- , --

Signed and Sealed this

Twenty-fifth Day of September, 2001

Attest:

NICHOLAS P. GODICI
*Attesting Officer*    *Acting Director of the United States Patent and Trademark Office*